(12) United States Patent
Zavitsanos et al.

(10) Patent No.: US 6,497,575 B2
(45) Date of Patent: Dec. 24, 2002

(54) SYSTEM AND METHOD FOR WHITENING TEETH

(76) Inventors: Peter D. Zavitsanos, 1218 Forest Hill Dr., Gwynedd Valley, PA (US) 19437; Robert J. Downs, Jr., 429 Gwynedd Valley Dr., Gwynedd Valley, PA (US) 19437

( * ) Notice: Subject to any disclaimer, the term of this patent is extended or adjusted under 35 U.S.C. 154(b) by 0 days.

(21) Appl. No.: 09/989,611

(22) Filed: Nov. 21, 2001

(65) Prior Publication Data

US 2002/0068260 A1 Jun. 6, 2002

Related U.S. Application Data

(63) Continuation-in-part of application No. 09/815,501, filed on Mar. 23, 2001, now abandoned.
(60) Provisional application No. 60/192,213, filed on Mar. 27, 2000.

(51) Int. Cl.[7] ................................................ A61C 5/00
(52) U.S. Cl. .......................................... 433/215; 433/32
(58) Field of Search .................................... 433/32, 215

(56) References Cited

U.S. PATENT DOCUMENTS

| | | | | |
|---|---|---|---|---|
| 1,084,017 | A | | 1/1914 | Lautenburg ................... 433/35 |
| 2,167,467 | A | | 7/1939 | Sisson ......................... 607/113 |
| 2,257,329 | A | * | 9/1941 | Britt ............................ 433/215 |
| 4,661,070 | A | | 4/1987 | Friedman ................. 433/203.1 |
| 4,983,381 | A | | 1/1991 | Torres Zaragoza .......... 433/215 |
| 5,165,424 | A | | 11/1992 | Silverman .................... 433/215 |
| 5,702,251 | A | | 12/1997 | McClintock, II ............ 433/215 |
| 5,889,257 | A | | 3/1999 | Schader et al. ............. 219/229 |
| 5,927,981 | A | | 7/1999 | Widen ......................... 433/215 |
| 5,980,249 | A | * | 11/1999 | Fontenot ..................... 433/215 |
| 6,102,705 | A | | 8/2000 | Darnell ....................... 433/216 |
| 6,382,979 | B2 | * | 5/2002 | Lindquist .................... 433/215 |

\* cited by examiner

*Primary Examiner*—John J. Wilson
(74) *Attorney, Agent, or Firm*—Klehr, Harrison, Harvey, Bransburg & Ellers LLP; John F. Letchford

(57) ABSTRACT

A teeth whitening system includes a heating module, a mouthpiece thermally connected to the heating module such that heat can be transferred to the mouthpiece, and a thermocatalytically activated whitening gel positioned in the mouthpiece such that the gel contacts a user's teeth, whereby when heat is transferred from the heating module to the mouthpiece, the gel is activated by heat, metal surface catalysis, and water or saliva to whiten the user's teeth.

13 Claims, 3 Drawing Sheets

SYSTEM AND METHOD FOR WHITENING TEETH

CROSS REFERENCE TO RELATED APPLICATIONS

This is a continuation-in-part application relating to U.S. application Ser. No. 09/815,501 filed Mar. 23, 2001, which is a §111(a) application and claims the benefit of to U.S. application Ser. No. 60/192,213 filed Mar. 27, 2000 (now abandoned).

FIELD OF THE INVENTION

The present invention relates to a system and method for whitening teeth, and, more particularly, to a system and method employing the use of heat and a delivery system which provides catalytic action thus accelerating the action of a bleaching medium.

BACKGROUND OF THE INVENTION

Whiter teeth are desired for cosmetic reasons, and several processes to accomplish this have been described in the prior art. These processes have always included the use of bleaching gels or solutions containing various concentrations of hydrogen peroxide ($H_2O_2$) or carbamide peroxide ($CH_6N_2O_3$), which on an equal molar basis contains 35% $H_2O_2$ (by weight) which is released from activation by water or other sources such as heat or light. The degree of whitening provided by these processes increases with (a) peroxide concentration, (b) time of contact between the reacting species of peroxide and the tooth enamel surface, (c) diffusion rate into the dentine layer, (d) a favorable structure (texture) of tooth surface, and most importantly, (e) the rate of activation of the gel in terms of generating available peroxide ($H_2O_2$) and/or its reactive species (OH and O). Due to its chemical structure, the peroxide must produce transient species such as OH and O before the final products, $H_2O$ and $O_2$, are generated by the following mechanism, $2\ H_2O_2 \rightarrow 4OH \rightarrow 2H_2O + 2O \rightarrow 2H_2O + O_2$. The presence of these active transient species (radical OH and atomic oxygen O) play the most important role in the whitening process due to their higher reactivity. In other words, two peroxide molecules must break down to four OH molecules, which react to produce two water ($H_2O$) molecules and two atoms of oxygen. The final step is the recombination of atomic oxygen into molecular oxygen.

In most cases, tooth whitening is accomplished with custom fitted plastic trays filled with bleaching gels (known as "take home trays") which are worn for one to several hours a day or overnight over extended periods of time such as several weeks or months before a satisfactory level of whitening is realized. Gel activation by light from laser sources or arc lamps in several regions of the electromagnetic spectrum, including infrared, visible, and ultraviolet, have been introduced with various and ambiguous levels of success due to: (a) lack of fundamental understanding of the mechanism involved in the whitening process, (b) lack of control in terms of the density of delivered energy, (c) the fraction of the energy absorbed by gel or absorbed by teeth, (d) shadowing effects, and (e) the necessity for prolonged periods of treatment if one tooth is treated at a time. (See, e.g., U.S. Pat. Nos. 4,952,143 and 4,661,070.)

Furthermore, some of the peroxide concentrations used (from 15% up to 30% $H_2O_2$) require effective gum isolation in order to prevent tissue burns. There is also a lack of information on the temperature that is generated by the light source and lack of temperature control. These factors can lead into gum burns, tooth sensitivity after the treatment, and possible long-term effects that are presently unknown.

Another method, U.S. Pat. No. 4,983,381, involves the use of applying heat directly to the teeth with a thermocube or plate, which covers the teeth. This method is difficult to implement and requires soft tissue isolation and protection due to high concentrations of $H_2O_2$ (30–70%) as well as requiring many steps and high temperatures (up to 55° C.). This design is also problematic because its close fit on the teeth does not allow enough volume for whitening gel. It also requires custom made plates (upper and lower arches) for each person.

Still another method, U.S. Pat. No. 5,927,981, utilizes a high temperature chamber for producing a high temperature (60° C.). In this method, a bleaching vapor is directed to the teeth from the chamber. This process is difficult to implement and exposes the recipient to unnecessary safety risks due to both the tooth pulp and the gums (if not isolated) being exposed to high temperatures. In addition, its whitening effectiveness is uncertain and further complicated by the fact that the transient species OH and O may no longer be present in the "bleaching vapor" when it reaches the teeth due to the length of travel.

The present invention provides a process which has the following advantages over the prior art: (a) lower peroxide concentrations (16% to 20% carbamide or 5 to 10% $H_2O_2$); (b) no gum isolation is required; (c) within one hour it can provide up to eleven shades of improvement, depending on age and level and type of coloration; (d) it provides greater comfort to recipient than take home trays or light activated whitening procedures; (e) it requires less peroxide over the course of the treatment than "take home trays;" and (f) it is safer than the light activation methods, especially those using high intensity lasers or other uncontrolled high intensity light sources, including those in the blue portion of the spectrum.

It should also be pointed out that this invention will accelerate the whitening process as well when the gel is confined by dentist-made take home trays or current office bleaching procedures which employ higher concentrations of hydrogen peroxide (30%) with isolation.

SUMMARY OF THE INVENTION

The present invention provides a safe and effective way for whitening teeth through a combination of new techniques, including a balanced and controlled delivery of activated bleaching medium. The present invention accelerates the action of the bleaching medium by increasing (a) the gel temperature; (b) the concentration of active peroxide species of the gel at the interface between the tooth surface and the attached gel; (c) the reaction rate between the active transient species (OH and O) of the peroxide and the coloring compounds in the teeth; and (d) the diffusion rate of the active species through the enamel. A heating wave is provided by a controlled thermal source which allows the temperature of the gel to reach a safe temperature range of 40°–42° C. on the tooth surface. The heating is also controlled by a combination of state of the art devices which control the temperature to ±1° C. or on a simpler approach by heat transfer.

In a first embodiment, the device includes a heating element embedded into an aluminum (or other metal or conductive material) cylinder referred to as a "heat sink" which is thermally insulated from the atmosphere with a plastic coating, highly insulating Styrofoam composite, or other insulator. The temperature of the heat sink is controlled and maintained at a level of 50°–65° C. so that a controlled, constant amount of thermal energy flows into a mouthpiece. The mouthpiece is made from metal, a metal matrix composite, or other thermally conductive material. The mouthpiece preferably includes a metallic substructure with a plastic/organic filler and a low conductivity coating or an open cell foam cover.

The heat sink temperature is controlled so that the temperature of the mouthpiece and the gel does not exceed a preset level (about 41° C.±1°). In case this temperature is exceeded in an electrically-powered embodiment, a safety thermocouple at the base of the mouthpiece automatically shuts off the power of the control box. For added safety, the heating element is electrically insulated from its case by ceramic cement and the case is also insulated from the heat sink by another layer of cement. The exteriors of heat sink and the mouthpiece are further insulated by plastic or Styrofoam coatings, thus providing a third level of safety. In addition, the demand of electric current(of the 30 watt heater at 120 V) is low and is limited to 0.25 amperes.

The increased effectiveness and speed of the whitening process is due to the faster generation and mobility of $H_2O_2$ in the peroxide gel, the decomposition of $H_2O_2$ to OH and O, the enhanced diffusion rate into the tooth as well as the enhancement of the reaction rate between the active peroxide species (which can be radicals of OH or atomic oxygen O) and the compounds on the enamel and dentine responsible for the stains and coloration. It is the change in the molecular state and bond structure (from double to single carbon bonds) of the coloring compounds which accounts for the lighter color, as well as the removal of stain compounds from the enamel surface.

The mouthpiece of the present invention is preferably made of a metal matrix composite consisting of a high conductivity, high heat-capacity metal skeleton (e.g., aluminum, copper, steel or other conductive alloy) that is surrounded by or impregnated with an open cell, porous, flexible foam. The mouthpiece may also be covered with a perforated plastic material. One important feature of this invention is based on the heat flow delivery from the heat sink, which is kept in the range of 50°–70° C. (depending on the relative size of heat sink to mouthpiece), to the metal matrix composite and is designed so that the foam temperature does not exceed levels of comfort or safety, which is in the vicinity of 41° C.

The method of the present invention controls the flow of thermal energy from a heat sink in order to provide thermal activation of bleaching gels. It accelerates the reaction of peroxide active species with pathological and normal colorations thus resulting in a faster whitening process via controlled heat flow, enhanced catalytic $H_2O_2$ decomposition by the metal mouthpiece and the fast transfer of reactionary ingredients through the open cell foam to the teeth. The advantages of the proposed methods are as follows: (a) temperature control at the base of the mouthpiece ensures safety by protection from overheating higher than 41° C., which is an acceptable safe level; (b) the conductive portion of the mouthpiece is isolated from the flesh of the mouth and the teeth; (c) it allows use of gels with lower peroxide concentrations which do not require protection and/or isolation of the gums through the application of coatings; (d) it works with a variety of hydrogen peroxide and/or carbamide peroxide gels, both hydrous and non-hydrous, the latter being more effective; (e) it provides a reservoir of peroxide sufficient to last at least a 30-minute treatment, to be repeated two or three times with new gel for best results; (f) the energy flow created by the heat sink as well as the construction of the mouthpiece provide the necessary balance required for the safety of the system; and (g) the flexible foam allows one size to fit all and its open cell structure allows easy transfer of more reactive species to travel from the metal side of the mouthpiece, which is hotter, to the tooth surface without raising the temperature of the tooth itself. This non-equilibrium event allows for even faster whitening results.

Other useful features of this invention include the fact that the metal component of the mouthpiece does not require plaster models to be made (to custom fit to the teeth) because it is large enough to fit most, if not all, mouth sizes due to the rigid metal front wall and the flexible foam or plastic back wall which provides the desirable fit around the teeth of any size or geometry. The construction of the mouthpiece is such that one mouthpiece can treat both upper and lower teeth simultaneously. The fact that the mouth is closed during treatment provides greater comfort to the recipient of the treatment, as compared to other methods based on light activation where the mouth is forced open with a lip retractor during the entire procedure. For several reasons (including safety and sanitary reasons), all or a portion of the metal matrix mouthpiece is designed to be disposable, such that it can be discarded at the end of the procedure.

BRIEF DESCRIPTION OF THE DRAWINGS

For a better understanding of the present invention, reference is made to the following detailed description of several exemplary embodiments considered in conjunction with the accompanying drawings, in which.

DETAILED DESCRIPTION OF THE INVENTION

Figure 1:
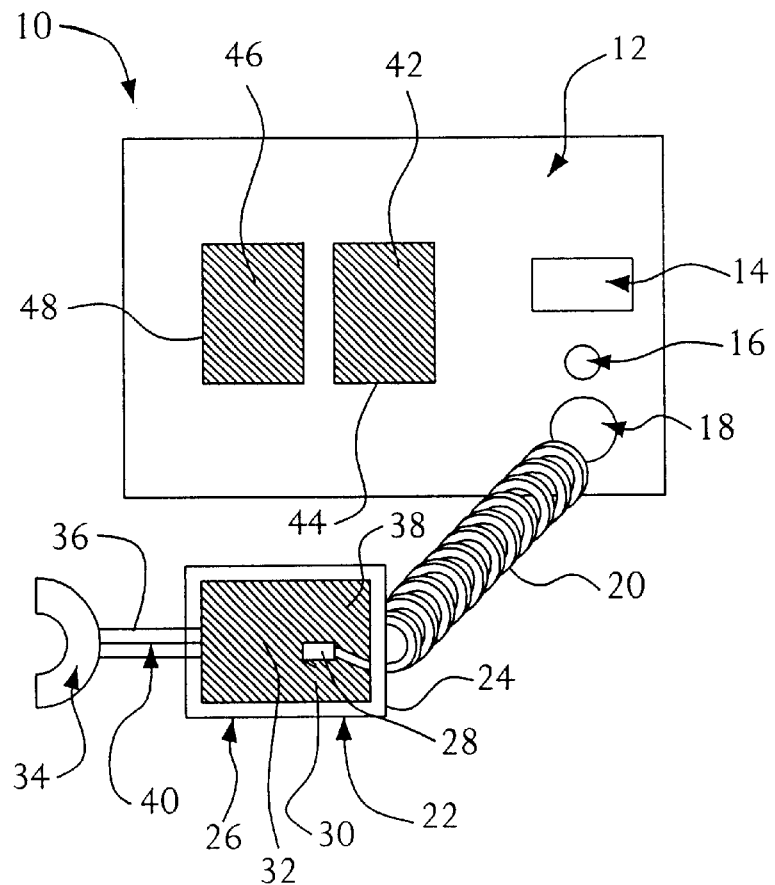
FIG. 1 is a block diagram of a first embodiment of a teeth whitening instrument constructed in accordance with the present invention.

A first, electrically-powered embodiment of a teeth whitening device 10 constructed in accordance with the present invention is shown in FIG. 1. The device 10 includes a control box 12, which houses a power and has a rectangular shape with sufficient room on the top or front side for several controls. An on/off switch 14 is located on the top of the control box 12 and is electrically connected to the power source. A replaceable fuse 16 is positioned inside the control box 12 and is electrically connected between the switch 14 and a connector 18. The connector 18 is used to connect a power cord 20 of a heating module 22 to the control box 12.

The heating module 22 consists of a case 24 having an outer layer 26 made of thermal insulation. A cartridge heater 28 is positioned inside the case 24 and is electrically connected to the power cord 20. A safety control 30 is electrically connected to the cartridge heater 28, in order to control the temperature of the cartridge heater 28. A heat sink 32 is electrically connected to the cartridge heater 28 such that the heat sink 32 retains heat generated by the cartridge heater 28. The heat sink 32 is a cylinder made of aluminum or other heat-conducting material which surrounds the heating element of the cartridge heater 28. The heat sink 32 is thermally insulated with an outer coating made of plastic, an insulating Styrofoam composite, or other insulating material.

A mouthpiece 34 is attached to the heating module 22 via a connector 36 which also provides heat flow to the mouthpiece 34 from the heat sink 32. A thermocouple 38, mounted in the heat sink 32, and a thermocouple 40, located in the connector 36, act together to regulate the temperature of the mouthpiece 34. If the temperature of the heat sink 32 exceeds the preset temperature range, the thermocouple 38 shuts off the power source in the control box 12, thereby preventing the heat sink 32 from heating further. Similarly, if the temperature of the mouthpiece 34 exceeds its preset level, the thermocouple 40 shuts off the power source in the control box 12, thereby preventing the mouthpiece 34 from heating further.

In order to accurately control the temperature of the mouthpiece 34, a number of controls are provided on the control box 12. The temperature of the heat sink 32 is indicated on a temperature display 42 and is adjusted by a controller 44. The temperature of the mouthpiece 34 is shown on a temperature display 46 and is pre-configured to approximately 41° C. A safety control 48, operating in conjunction with the safety control 30 in the heating module 22, is used to maintain the temperature of the mouthpiece 34 within a tolerance of ±1° C., such that the temperature of the mouthpiece 34 is within a range of 40°–42° C.

Figure 2:
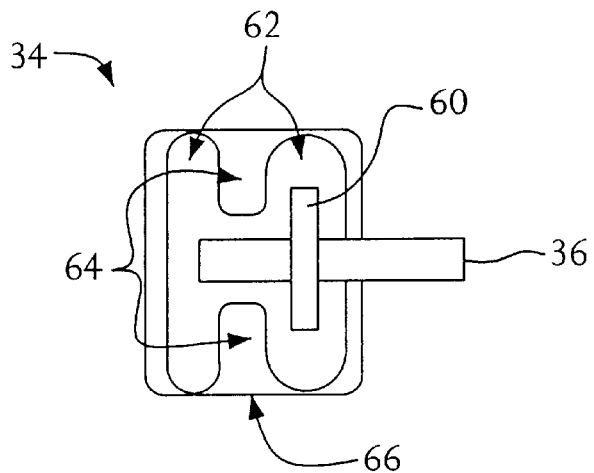
FIG. 2 is a cross-sectional side view of a mouthpiece used in connection with the various embodiments of the present invention.

FIG. 2 shows details of the construction of the mouthpiece 34. The connector 36, which is removably attached at one end to the heat sink 32, is fixedly attached at an opposite end to a metallic substructure 60 that forms the "backbone" of the mouthpiece 34. The connector 36 may be force-fit or friction-fit into the heat sink 32, or may be removably connected to the heat sink 32 by any conventional means. Some illustrative examples of a removable connection between the connector 36 and the heat sink 32 will be described below in connection with FIG. 3. A tooth form 62, composed of molded foam or plastic, surrounds the metallic substructure 60 and is designed to transfer heat from the metallic substructure 60 to a user's teeth.

The tooth form 62 can be constructed as fitting either the upper or lower teeth only, or as fitting both the upper and lower teeth simultaneously. In a preferred embodiment, the tooth form 62 is constructed of an open cell, porous foam. When in use, the tooth form 62 is first moistened with water and a heat-activated gel 64 is placed in the tooth form 62, whereby the gel 64 coats the user's teeth. The mouthpiece 34 can be manufactured to already include the gel 64 in the tooth form 62; in such circumstances, a seal 66 is provided around the tooth form 62 to retain the gel 64 therein and to preserve the sterility of the mouthpiece 34.

In a preferred embodiment, the open cell foam used to make the tooth form 62 provides a protective buffer for the user's teeth and allows the reactive species of hydrogen peroxide to flow freely between the metallic substructure 60 and the user's teeth. Water, which is pre-applied to the tooth form 62, together with the user's saliva acts to (i) enhance the conduction of heat from the tooth form 62 to the gel 64, and (ii) break down a non-hydrous peroxide gel. This process allows the gel 64 to be heated by the metallic substructure 60 at higher temperatures (50°–60° C.) than exist on the outside of the tooth form 62. The higher temperatures and the presence of water increase the reactivity of the peroxide gel and accelerates the whitening process.

The following discussion of the operation of the present invention assumes that the mouthpiece 34 is attached to the cartridge heater 28 and the seal 66, if present, has been removed. First, the user inserts the mouthpiece 34 into his or her mouth, with the tooth form 62 surrounding the teeth, permitting the gel 64 to coat the teeth. The user then moves the switch 14 to the "on" position, which begins heating the heat sink 32 to a temperature of between 75°–80° C. The heat is transferred from the heat sink 32 to the metallic substructure 60, such that the tooth form 62 is heated to a temperature of approximately 41° C. The safe temperature range for both the activation of the gel 64 and the safety of the user's teeth and gums is between 40°–42° C. At higher temperatures, there is a risk of burning the user's gums. While the mouthpiece 34 is in position, the user can place the case 24 on his or her chest (or through a brace), so that the user does not have to hold the case 24 during the entire length of the procedure. Another arrangement is to position the mouthpiece perpendicular to the heat sink (i.e., attached to the side).

The gel 64 is of a type that has a low peroxide concentration (e.g., 16%–20% carbamide or 5%–10% $H_2O_2$). Either hydrous or non-hydrous peroxide gels can be used effectively with the present invention. Improved results can be attained by using a non-hydrous gel, because in addition to enhancing the conduction of heat (increasing the reaction rate), the water applied to the tooth form 62 mixes with and attacks the non-hydrous peroxide gel 64, further accelerating the reaction rate and the whitening process. Using a gel 64 having high viscosity and low peroxide concentration avoids having to isolate the user's gums to prevent burns.

The combination of the gel 64, the temperature of the mouthpiece 34, and the time the mouthpiece 34 is worn (approximately a total of one hour in 20 or 30-minute segments with gel replacement), can provide up to eleven shades of whitening. The increased effectiveness and speed of the whitening process is due to the faster generation and mobility of $H_2O_2$ in the peroxide gel 64 as well as the enhancement of the reaction rate between the active peroxide species (which can be radicals of OH and atomic oxygen O) and the compounds on the enamel and dentine responsible for the stains and coloration. It is the change in the molecular state and bond structure (from double to single carbon bonds) of the coloring compounds in dentine which accounts for the lighter color as well as the removal of staining substance from the enamel surface.

One of the important features of the present invention is the open cell structure of the foam on the tooth form 62 of the mouthpiece 34, which allows some of the gel 64 to come into contact with the metal substructure 60 of the mouthpiece 34, which, due to the higher temperature of the metal, generates transient species of OH and O at a faster rate than would otherwise be achieved without contacting the metal. The open cell foam material can be attached to the substructure 60 by blowing, molding, or bonding with an adhesive.

The use of an open cell foam for the tooth form 62 is important because the metal substructure 60 of the mouthpiece 34 maintains a higher temperature (between 50°–60° C.) than the teeth can tolerate and therefore allows for a faster generation of active ingredients at the interface between the metal and the foam. The thermally generated active ingredients can flow through the open cell foam to the teeth surface and provide a faster bleaching action. This process is based upon a beneficial non-equilibrium event since the active ingredients (OH and O) were generated at a higher temperature than the temperature of the tooth surface, thereby providing for enhanced whitening action without discomfort or safety concerns due to the drop in temperature at the exterior of the tooth form 62.

Applying water to saturate the open cell foam is important for two reasons. First, the water acts as a heat conductor, enhancing the reaction rate of the gel. Second, when a non-hydrous peroxide gel is used, the water mixes with and attacks the gel to generate the transient species faster. The water, which is pre-applied to the open cell foam, acts together with the user's saliva, the heat, and a non-hydrous peroxide gel to accelerate the bleaching process. This process allows the use of more gel because the reaction rate is increased, and as a result, the contact time of the reactive species with the user's teeth is increased. Another advantage of this device is based on the catalytic action of the hot metal surface. The mouthpiece may have a rough aluminum surface or may be coated with other metals such as platinum, palladium, and other known catalysts which can catalytically enhance the generation of active species even further.

The electrically-powered embodiment of the present invention provides redundant controls in several ways in order to prevent exposing the patient to higher temperatures than those which are physiologically experienced by the body (such as fever or drinking coffee), and to reduce the possibility of electric shock from the heating element. The temperature of the mouthpiece 34 is monitored and controlled by the two thermocouples 38, 40, which are located in two different positions. The thermocouple 38 monitors the temperature at the heat sink 32 and shuts off the power when the preset temperature is exceeded and the thermocouple 40 monitors the temperature at the front of the mouthpiece 34 and shuts off the power if the temperature exceeds the safety zone, even by one degree. The heating element of the cartridge heater 28 is electrically isolated from the heat sink 32 by two layers of insulation, preferably made of ceramic cement: one between the electrically heated element and the exterior of the cartridge heater 28, and another between the exterior of the cartridge heater 28 and the heat sink 32. The metallic substructure 60 of the mouthpiece 34 is also insulated from direct contact with the human flesh or teeth.

The advantages of the teeth whitening device 10 include: (a) the thermocouple 40 in the connector 36 to the mouthpiece 34 helps to prevent overheating the mouthpiece 34 higher than the preferred 41° C. level; (b) the heating element of the cartridge heater 28 is electrically isolated from the exterior of the case 24 and the exterior of the cartridge heater 28 is electrically isolated from the heat sink 32; (c) the metallic substructure 60 of the mouthpiece 34 is isolated from the flesh of the mouth and the teeth; (d) the use of a variety of gels 64 with low peroxide concentrations, which do not require protection and/or isolation of the gums through the application of coatings; (e) providing a reservoir of gel 64 sufficient to last throughout the process (approximately one hour) without re-application of gel; and (f) the energy flow created by the heat sink 32, as well as the construction of the mouthpiece 34, provide safety balance.

Figure 3:
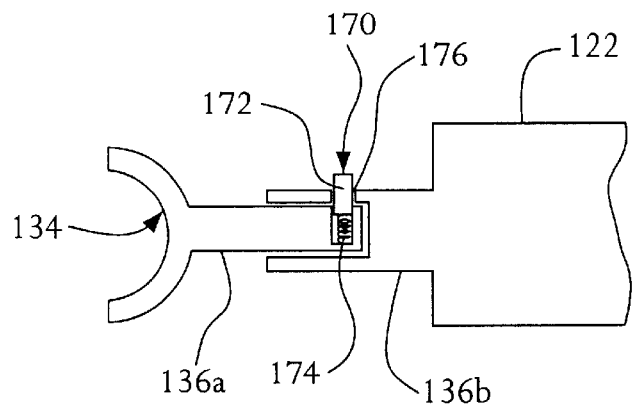
FIG. 3 is a top view, in partial cross-section, of an alternate embodiment of the connection between the mouthpiece and the heating module shown in FIG. 1.

Another exemplary embodiment of a mouthpiece constructed in accordance with the present invention is illustrated in FIG. 3. Elements illustrated in FIG. 3 which correspond to the elements described above with respect to FIGS. 1 and 2 have been designated by corresponding reference numerals increased by one hundred. The embodiment of FIG. 3 is designed for use in the same manner as the embodiment of FIGS. 1 and 2 unless otherwise stated.

Referring now to FIG. 3, an alternate configuration for locking the mouthpiece 134 to the heating module 122 is shown. The connector 136 has two portions: a first portion 136a fixedly attached to the mouthpiece 134 and a second portion 136b fixedly attached to the heating module 122. The first portion 136a and the second portion 136b are releasably connected via a locking mechanism 170. The locking mechanism includes a pin 172 biased by a spring 174, both of which are mounted in the first portion 136a opposite the mouthpiece 134. The pin 172 engages an opening 176 in the second portion 136b to lock the first portion 136a within the second portion 136b. To separate the first portion 136a from the second portion 136b, the user pushes on the pin 172 to pass it through the opening 176, which permits the first portion 136a to slide within and relative to the second portion 136b. Being able to separate the mouthpiece 134 from the heating module 122 allows the mouthpiece 134 to be easily cleaned or discarded.

In addition to the locking mechanism 170, the mouthpiece 134 may be connected to the heating module 122 by any other conventional means, such as, for example, inserting a set screw through the opening 176 so that it engages the first portion 136a or by threadedly connecting the mouthpiece 134 to the heating module 122.

In addition to providing the heating by electrical means, other heating mechanisms are also effective. These include: (a) immersing the heat sink 32 in hot water (see the discussion in connection with FIG. 4 below), (b) heating the heat sink 32 by using a hot plate or other heating device that can be controlled such that its temperature does not exceed 100° C., (c) heating the mouthpiece 34 by hot water through a hollow construction of an appendix heat sink manually or with a pump, (d) making the heat sink 32 out of a porous ceramic (or plastic) filled with water and heating in a microwave oven, (e) preheating a hermetically sealed mouthpiece 34 with gel 64 in hot water or in a microwave oven, and (f) encapsulating an inorganic salt or other material which changes phase from solid to liquid at warm water temperatures 55°–70° C. into the heat sink. This phase change process is endothermic and the process is reversed during cooling, as the liquid converts into solid with the release of the heat of fusion. This allows the heat sink to cool down slower and thus mitigate the need for multiple heating steps during the procedure.

These alternates may also be safely used by consumers in their homes, as opposed to use by dental professionals in their offices. The alternate designs of these devices provide the advantages of lower cost heat activated teeth whitening without the need for an electrically powered device, of a one hour procedure and still whitening all teeth with a single mouthpiece, and no tissue isolation.

Figure 4:
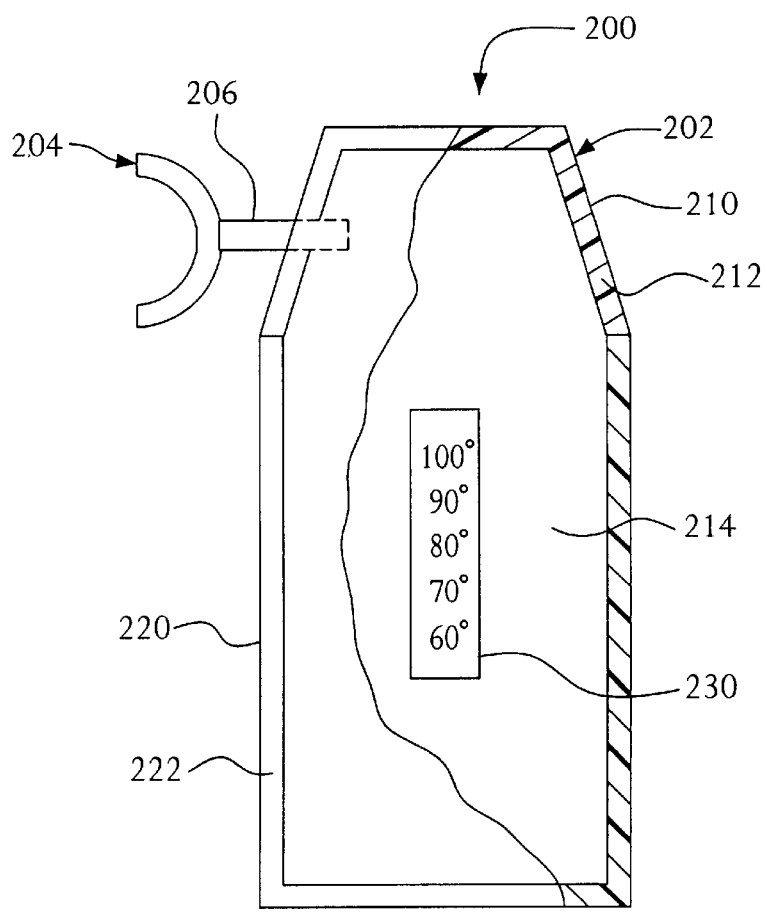
FIG. 4 is a partial cross-sectional side view of a second embodiment of a teeth whitening instrument constructed in accordance with the present invention.

An example of an embodiment of the present invention adapted for home use is shown in FIG. 4. A teeth whitening device 200 includes a heating unit 202 and a mouthpiece 204 with a stem 206. The mouthpiece 204 is attached to the heating unit 202 by the stem 206. The mouthpiece 204 is preferably constructed in the same manner as the mouthpiece 34 shown in FIG. 2. The heating unit 202 has an upper portion 210 with an exterior insulating layer 212 and a heat sink 214 attached to the interior of the insulating layer 212. The stem 206 extends through the insulating layer 212 and contacts the heat sink 214, which is made of a thermally conducting material, such as aluminum. A lower portion 220 of the heating unit 202 is removably attached to the upper portion 210 and has an insulating layer 222 and a hollow interior sized and shaped to snugly fit around the heat sink 214. A temperature indicating strip 230 is affixed to the exterior of the heat sink 214 and displays the temperature of the heat sink 214 when heated, as described in greater detail below.

To heat the heat sink 214 to the desired operating temperature, the lower portion 220 is detached from the upper portion 210 of the heating unit 202, thereby exposing a portion of the heat sink 214. In a separate container (e.g., a pot), water is brought to a boil and the exposed portion of the heat sink 214 is placed into the boiling water. In several minutes of such heating, the heat sink 214 reaches a temperature of 90–100° C. At that point, the heating unit 202 is removed from the water and the lower portion 220 is placed around the heat sink 214 and is attached to the upper portion 210, completely insulating the heat sink 214, so that the heating unit 202 is safe to handle. The balance in heat flow from the heat sink 214 to the mouthpiece 204 is such that the gel temperature at the tooth surface does not exceed 41° C.

The heat sink 214 is heated to 90°–100° C. by boiling water, hot plate, or other heating means. The temperature of the heat sink 214 is indicated by the temperature indicating strip 230 affixed to the heat sink 214. The temperature strip 230 changes color to indicate the change in temperature. When boiling water is used as the heat source, the temperature of the heat sink 214 will not exceed 100° C. So long as the initial temperature of the heat sink 214 is between 90°–100° C., the temperature of the metal substructure of the mouthpiece 204 will be between 50°–60° C. and the temperature of the foam covering of the mouthpiece 204, which is the part of the mouthpiece 204 that comes into contact with the user's teeth, will be maintained at 40°–41° C.

Once the heat sink 214 reaches a temperature of between 90°–100° C., it is removed from the heating source, inserted to the lower portion of the insulating cover, and is ready to be used as part of the teeth whitening process. The mouthpiece 204 is then inserted into the heat sink 214, from which it draws thermal energy. After assembly, the device 200 provides a steady, controlled flow of heat to the mouthpiece 204. The flow of heat from the heat sink 214 to the mouthpiece 204 is controlled by (i) the temperature of the heat sink 214, (ii) the size of the heat sink 214, (iii) the length and thickness of the connector 206, and (iv) the surface area of the portion of the connector 206 that is inserted into the heat sink 214. The temperature of the mouthpiece 204 is maintained within a tolerance of ±1° C., such that the temperature of the mouthpiece 204 is within a range of 40°–42° C., although in this version, the temperature will continue to drop during treatment.

Depending on the thickness of the insulating layers 212, 222 surrounding the heat sink 214, the teeth whitening device 200 will provide useful thermal activation for up to 20–30 minutes. The heating process must be repeated two-three times, with new gel each time, in order to provide an effective treatment. This embodiment provides initial whitening and allows for "touch-up" treatments perhaps two to three times a year.

Figure 5:
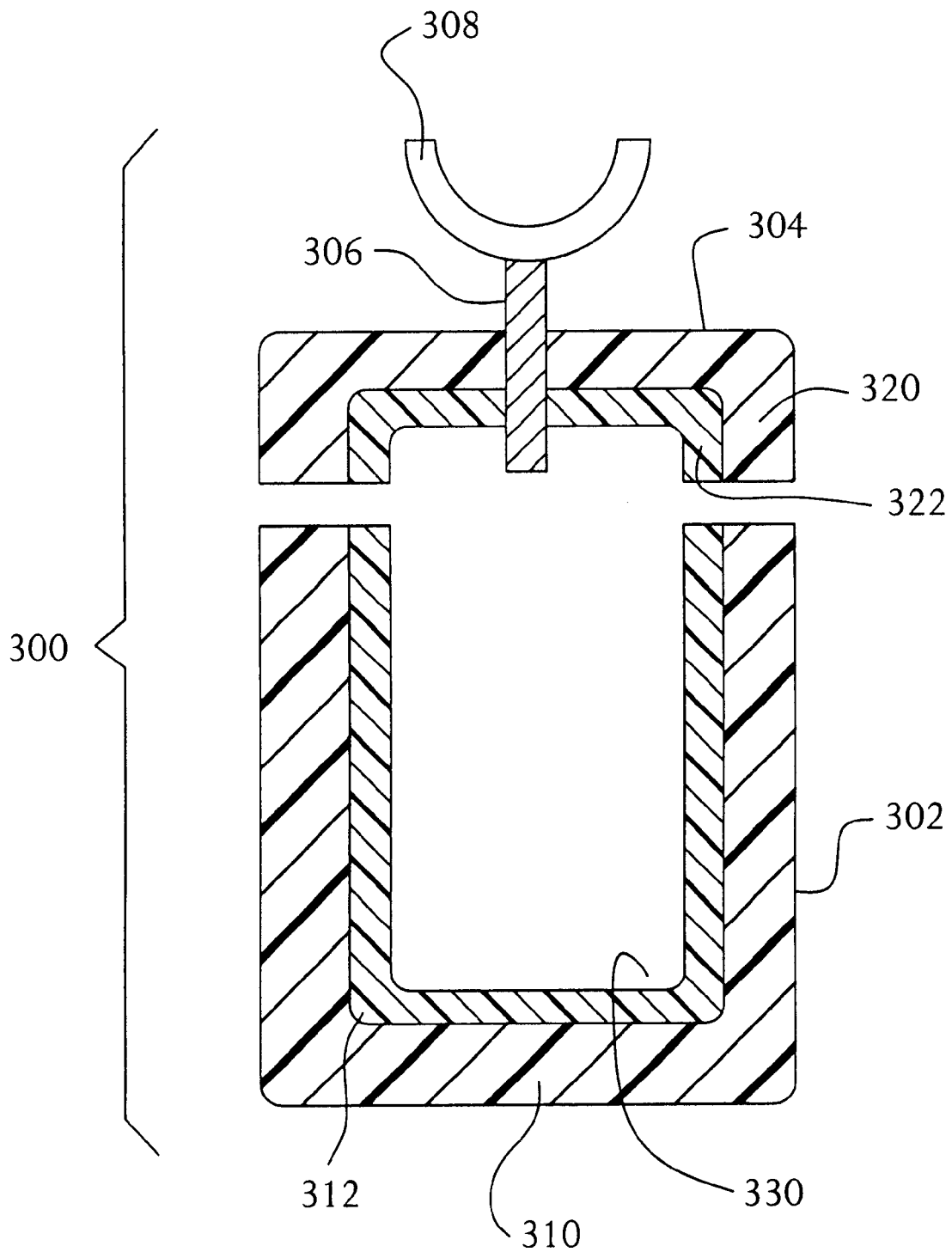
FIG. 5 is a cross-sectional side view of a third embodiment of a teeth whitening instrument constructed in accordance with the present invention.

FIG. 5 shows another alternate embodiment of the present invention adapted for home use. A teeth whitening device 300 includes a lower portion 302 and an upper portion 304, which fit together to form a closed container. A connector 306 extends through the upper portion 304 and a mouthpiece 308 is fixed to one end of the connector 306, external to the upper portion 304. The lower portion 302 is formed as a hollow cylinder having an outer insulating layer 310 made of Styrofoam or other insulating material and an inner layer 312 made of plastic. The upper portion 304 includes an outer insulating layer 320 made of Styrofoam or other insulating material and an inner layer 322 made of plastic. The lower portion 302 and the upper portion 304 relate together such that the respective inner layers 312, 322 form a single chamber 330.

To use the teeth whitening device 300, the upper portion 304 is separated from the lower portion 302, and the lower part of the chamber 330 is filled with a liquid, such as water, water mixed with sodium chloride, sodium acetate, or other microwaveable liquid. The lower portion 302 is placed into a microwave oven to heat the liquid. After the liquid is heated, the lower portion 302 is removed from the microwave oven and the upper portion 304 is attached thereto, thereby sealing the device 300 and completely containing the heated liquid in the chamber 330. Heat from the liquid is transferred to the mouthpiece 308 through the connector 306.

EXAMPLES OF PERFORMANCE

The electrically heated/controlled version of the present invention was used by the inventors on eighteen subjects with results ranging in shade change from three to ten. The shade levels and the shade change are based upon measurements taken from the VITAPAN classical guide, produced by Vident of Brea, Calif. The gel contained 20% carbamide peroxide, treatment times varied from 35–60 minutes, and the age of the subjects ranged from 24–68 years. The results of this study are shown in Table 1.

TABLE 1

Effectiveness Data.

| Subject | Age | Treatment Time (minutes) | Shade Before | Shade After | Shade Change |
|---------|-----|--------------------------|--------------|-------------|--------------|
| 1 | 68 | 60 | B4 | B2 | 10 |
| 2 | 37 | 50 | B3 | A1 | 9 |
| 3 | 64 | 50 | B4 | D4 | 5 |
| 4 | 37 | 45 | A2 | <B1 | 3 |
| 5 | 36 | 40 | A2 | B1 | 3 |
| 6 | 40 | 35 | A3 | B2 | 6 |
| 7 | 39 | 60 | D3 | B2 | 7 |
| 8 | 65 | 40 | A35 | C1 | 6 |
| 9 | 58 | 60 | B4 | D4 | 5 |
| 10 | 47 | 55 | A3 | C2 | 5 |
| 11 | 42 | 40 | A3 | A2 | 5 |
| 12 | 49 | 40 | C1 | B2 | 3 |
| 13 | 28 | 40 | A35 | B2/A1 | 9–10 |
| 14 | 42 | 50 | B3 | C1 | 5 |
| 15 | 43 | 50 | D4 | B2 | 5 |
| 16 | 49 | 60 | A35 | B2 | 9 |
| 17 | 55 | 60 | C4 | A35 | 4 |
| 18 | 35 | 40 | C4 | A3 | 7 |

In addition to the tests conducted by the inventors, a similar study was funded by the inventors and conducted by the University of Buffalo School of Dental Medicine. The results of this study involved twenty subjects. Ten were treated with the present invention and a 3% hydrogen peroxide gel; ten were treated solely with the same gel. These results confirmed the effectiveness of the present invention in that under exactly the same conditions in two 30-minute treatments, the present invention produced whiter teeth by 4–5 shades higher than the gel alone. The lower concentration gel (3% hydrogen peroxide) produced up to seven shade changes as compared to ten shade changes with the 20% carbamide peroxide gel.

Trials by the inventors involving the embodiment shown in FIG. 4 yielded similar results. The major difference between the two embodiments being that the heat sink needs to be reheated by boiling water 2–3 times for 20–30 minute treatments in order to achieve equivalent results. In fact, in one case, the take-home unit using 20% carbamide peroxide gel and two 40-minute treatments resulted in a total of 11 shades improvement.

It will be understood that the embodiments described herein are merely exemplary and that a person skilled in the art may make many variations and modifications without departing from the spirit and scope of the present invention. All such variations and modifications are intended to be included within the scope of the invention as defined in the appended claims.

What is claimed is:

1. A mouthpiece for use in a teeth whitening system, comprising:
    a substructure having a rough surface for enhancing chemical reactions that cause teeth to whiten;
    a connector attached to said substructure, said connector sized and shaped to interface with the teeth whitening system; and
    a tooth form carried by said substructure opposite said connector.

2. A mouthpiece according to claim 1, wherein said substructure is made of metal.

3. A mouthpiece according to claim 1, wherein said substructure is made of metal composite.

4. A mouthpiece according to claim 1, wherein said tooth form is sized and shaped to fit at least one of the upper set of teeth and the lower set of teeth of a user.

5. A mouthpiece according to claim 1, wherein said tooth form is made of molded foam.

6. A mouthpiece according to claim 5, wherein the molded foam is an open cell, porous foam.

7. A mouthpiece for use in a teeth whitening system, comprising:
    a substructure coated with a catalyst for enhancing chemical reactions that cause teeth to whiten;
    a connector attached to said substructure, said connector sized and shaped to interface with the teeth whitening system; and
    a tooth form carried by said substructure opposite said connector.

8. A mouthpiece according to claim 7, wherein said substructure is made of metal.

9. A mouthpiece according to claim 7, wherein said substructure is made of metal composite.

10. A mouthpiece according to claim 7, wherein said tooth form is sized and shaped to fit at least one of the upper set of teeth and the lower set of teeth of a user.

11. A mouthpiece according to claim 7, wherein said tooth form is made of molded foam.

12. A mouthpiece according to claim 11, wherein the molded foam is an open cell, porous foam.

13. A method for whitening teeth comprising the steps of:
    charging a thermally-chargeable heat sink to a desired operating temperature by a heating source;
    removing the heat sink from the heating source; and
    inserting a mouthpiece connected to the heat sink into a mouth of a user, wherein the mouthpiece has applied thereto a heat-activated whitening agent, whereby heat flows from the heat sink to the mouthpiece and the heat activates the whitening agent to whiten a user's teeth.

* * * * *